United States Patent
Heuer et al.

(10) Patent No.: US 9,676,716 B2
(45) Date of Patent: Jun. 13, 2017

(54) POLYCARBONATE HAVING IMPROVED THERMAL AND MECHANICAL PROPERTIES AND REDUCED COEFFICIENTS OF THERMAL EXPANSION

(75) Inventors: Helmut-Werner Heuer, Krefeld (DE); Rolf Wehrmann, Krefeld (DE)

(73) Assignee: Covestro Deutschland AG, Leverkusen (DE)

(*) Notice: Subject to any disclaimer, the term of this patent is extended or adjusted under 35 U.S.C. 154(b) by 670 days.

(21) Appl. No.: 12/973,060

(22) Filed: Dec. 20, 2010

(65) Prior Publication Data

US 2011/0151262 A1    Jun. 23, 2011

(30) Foreign Application Priority Data

Dec. 21, 2009  (DE) .................. 10 2009 059 771

(51) Int. Cl.
| | |
|---|---|
| *C07D 209/46* | (2006.01) |
| *C08G 64/12* | (2006.01) |
| *C08G 73/00* | (2006.01) |
| *C08J 7/12* | (2006.01) |
| *B29C 47/00* | (2006.01) |
| *B29K 69/00* | (2006.01) |

(52) U.S. Cl.
CPC ........ *C07D 209/46* (2013.01); *B29C 47/0009* (2013.01); *C08G 64/12* (2013.01); *C08G 73/00* (2013.01); *C08J 7/123* (2013.01); *B29K 2069/00* (2013.01); *Y10T 428/31507* (2015.04)

(58) Field of Classification Search
CPC .......... C08G 64/12; C08G 73/00; C08J 7/123; B29K 2069/00; B29C 47/0009; Y10T 428/31507
See application file for complete search history.

(56) References Cited

U.S. PATENT DOCUMENTS

| | | |
|---|---|---|
| 4,898,896 A | 2/1990 | Maj et al. |
| 5,344,910 A * | 9/1994 | Sybert ................... 528/201 |
| 5,672,645 A | 9/1997 | Eckel et al. |
| RE36,902 E | 10/2000 | Eckel et al. |
| 6,355,723 B1 | 3/2002 | van Baal et al. |
| 7,358,321 B2 | 4/2008 | Mahood et al. |
| 2007/0123712 A1* | 5/2007 | Ganesan et al. ........... 548/476 |
| 2008/0081896 A1* | 4/2008 | Heuer ...................... 528/196 |
| 2008/0274360 A1* | 11/2008 | Gallucci ............ C08F 283/00 428/412 |
| 2009/0030171 A1* | 1/2009 | Leenders ............ C08L 69/00 528/196 |

FOREIGN PATENT DOCUMENTS

| | | |
|---|---|---|
| DE | 1031512 B | 6/1958 |
| EP | 0313436 A1 | 4/1989 |
| EP | 0363608 A1 | 4/1990 |
| EP | 0553581 A2 | 8/1993 |
| EP | 0585056 A2 | 3/1994 |
| EP | 0640655 A2 | 3/1995 |
| EP | 0725101 A1 | 8/1996 |
| EP | 0863180 A1 | 9/1998 |
| EP | 0913421 A1 | 5/1999 |
| EP | 1312647 A2 | 5/2003 |
| WO | WO-99/55772 A1 | 11/1999 |
| WO | WO-2008/121149 A1 | 10/2008 |

OTHER PUBLICATIONS

Adamczyk, M., et al., "A Practical Method for the Synthesis of Phenophthalein Spirolactams," Organic Preparations and Procedures International, vol. 33, No. 1, pp. 95-100 (2001).
Loewe, S., "Studies on the Laxative Activity of Triphenylmethane Derivatives: I. Relationship Between Structure and Activity of Phenolphthalein Congeners," Journal of Pharmacology and Experimental Therapeutics, vol. 94, No. 3, pp. 288-298 (1948).
Morgan, P. W., "Linear Condensation Polymers from Phenolphthalein and Related Compounds," Journal of Polymer Science: Part A, vol. 2, pp. 437-459 (1964).
Küper et al., "Vacuum Deposition of Functional Coatings on Polymer Substrates, Technical Properties and Manufacturing Aspects", 14 pages, dated Nov. 25, 2006.

* cited by examiner

*Primary Examiner* — Callie Shosho
*Assistant Examiner* — John Freeman
(74) *Attorney, Agent, or Firm* — Drinker Biddle & Reath LLP

(57) ABSTRACT

The present invention relates to thermoplastic high-Tg polycarbonates and molding materials which are distinguished by improved thermal properties and improved mechanical properties, in particular by reduced thermal expansion. The present invention furthermore relates to a process for the preparation of these polycarbonates. In particular, this invention relates to polycarbonates which the structural unit which derives from phthalimide of the formula (I) and polycarbonate compositions and molding materials therefrom as well as a process for the preparation of these polycarbonates, and the use thereof, in particular as reflectors and display substrates.

12 Claims, 1 Drawing Sheet

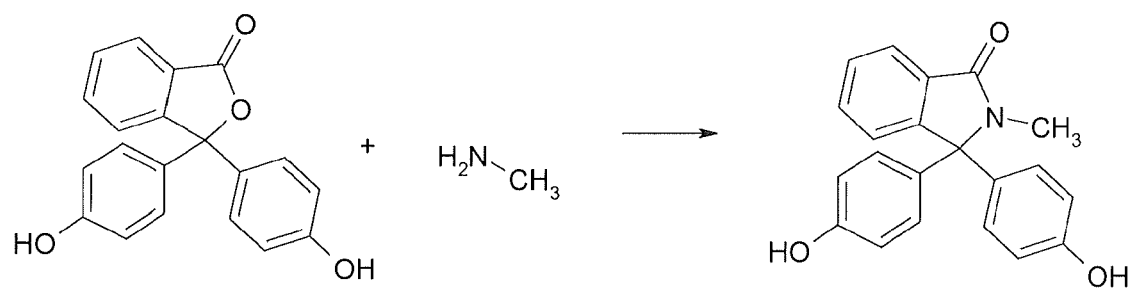

POLYCARBONATE HAVING IMPROVED THERMAL AND MECHANICAL PROPERTIES AND REDUCED COEFFICIENTS OF THERMAL EXPANSION

RELATED APPLICATIONS

This application claims benefit to German Patent Application No. 10 2009 059 771.9, filed Dec. 21, 2009, which is incorporated herein by reference in its entirety for all useful purposes.

BACKGROUND OF THE INVENTION

The present invention relates to thermoplastic high-Tg polycarbonates and moulding materials which are distinguished by improved thermal properties and improved mechanical properties, in particular by reduced thermal expansion. The present invention furthermore relates to a process for the preparation of these polycarbonates. In particular, this invention relates to polycarbonates which the structural unit which derives from phthalimide of the formula (I) and polycarbonate compositions and moulding materials therefrom as well as a process for the preparation of these polycarbonates, and the use thereof, in particular as reflectors and display substrates.

(Co)polycarbonates belong to the group consisting of the industrial thermoplastics. They have a wide range of uses in the electrical and electronic sector, as housing material of lights and in applications where both particular thermal and mechanical properties and outstanding optical properties are required, for example applications in the automotive sector, plastic covers, diffuser screens or waveguide elements and lamp covers, lamp bezels. Reflectors or subreflectors produced from a thermoplastic by injection moulding with outstanding surface quality would have been a very interesting addition to these applications for (co)polycarbonates.

In these applications, the good thermal properties such as Vicat temperature (heat distortion resistance) and glass transition temperature, are virtually always essential. Good adhesion to metal, for example to aluminium, is also indispensable for some applications. At the same time, outstanding optical properties are of the greatest importance. To date, mechanical properties with regard to thermal expansion of the amorphous polycarbonate with constant thermal properties, such as the coefficient of linear thermal expansion, remain unconsidered.

Thermoplastics from which light-reflecting components are produced by injection moulding and subsequent metallization (vacuum coating, generally with aluminium) are known. Such components are, for example, headlamp reflectors for automobiles. In addition to the paraboloid headlamps previously used without exception, two basic types optimized with regard to light utilization and space requirement were developed, the projection headlamp (ellipsoid, polyellipsoid) and the free-surface headlamp. Since, owing to the optimized light utilization and distribution of this reflector type, the lenses, in particular of free-surface headlamps can generally be designed without a profile, clear polycarbonate lenses are used today. This increases the requirements regarding the surface quality of the elements clearly visible from the outside (e.g. reflector, subreflector, frame), the dimensional stability at elevated temperature, little gas emission to avoid bubble formation, the mechanical strength, easy processing and low manufacturing tolerances furthermore being important.

To date, headlamp reflectors have been produced either from sheet metal or metallized injection moulded parts comprising thermosetting plastic (bulk moulding compounds, BMC). Good dimensional stability and thermal stability are required here.

Headlamp reflectors can also be divided into the actual reflector essentially having a paraboloid shape and a subreflector differing to a greater or lesser extent from the paraboloid shape. The reflector is the actual component which reflects the light in a targeted manner for the desired illumination and which is usually arranged in the immediate vicinity of the light-producing incandescent lamp. The lamp or incandescent bulb or light source corresponding to these produces not only light but also heat so that the reflector may be exposed to an operating temperature of about 180-220° C., depending on design. For this reason, it is necessary to provide materials having a coefficient of linear thermal expansion as low as possible. This material should be capable of being processed as far as possible by injection moulding technology and should be economical.

In addition, the reflectors should be dimensionally stable in a temperature range from −50° C. to 220° C., i.e. the expansion and shrinkage behaviour must as far as possible be isotropic so that—at least in the case of the reflector—the luminous efficiency or light focussing is not adversely affected. Preferably, the metal layers have substantially the same expansion and shrinkage behaviour as the reflectors, so that the tensile or shear stress of the reflection layers is as small as possible. As a result, the danger of cracking or compression in the reflection layers is additionally reduced.

In general, thermosetting plastics, more rarely also thermoplastics, have been used to date for producing reflectors. Of the latter, the amorphous thermoplastics mainly used, e.g. polyetherimide (PEI), polyamidimide (PAI) or polysulphones, e.g. polyether sulphone (PES) or polysulphone (PSU) or polyphenylene ether sulphone (PPSU), have a high to very high glass transition temperature (Tg) (cf. for example PAI TORLON® from Solvay Advanced Polymers). These amorphous high-Tg thermoplastics can be used without fillers for producing reflector blanks having outstanding surface smoothness. Reflector blanks can be directly metallized. A disadvantage for mass production is, however, the very high cost of said amorphous high-Tg thermoplastics in some cases. Moreover, the processing of some of these high-Tg thermoplastics is difficult.

For headlamp reflectors, mainly bulk moulding compounds (BMC) have been used for some time. These are the semifinished fibre-matrix product. It generally consists of short glass fibres and a polyester or vinyl ester resin; other reinforcing fibres or resin systems are possible. BMC is processed in the hot pressing process, which permits short cycle times. For this purpose, the BMC material is inserted centrally into a heated, divided mould. On closing, the BMC is distributed in the mould. Owing to the short fibre lengths, thin ribs and wall thicknesses can also be filled during pressing. However, there is the danger that the BMC will separate at constrictions. This occurs when a constriction is blocked by fibres so that only the resin can flow onwards. The individual reinforcing fibres are as a rule oriented in the direction of flow, so that locally highly oriented fibres may occur. In special processes, BMC, with appropriately small fibre lengths, can also be processed in the injection moulding process.

A typical application for thermosetting plastics (BMC) comprises car headlamps, more precisely the reflectors of the headlamp. The good dimension stability and thermal stability play a role here. The process resembles to a very great extent elastomer injection moulding. The cycle times in the processing of thermosetting plastics is as a rule longer than in the case of thermoplastics at wall thicknesses up to about 4 mm. As a result, thermosetting plastics are generally inferior to the thermoplastics in a cost-efficiency comparison if the good electrical and mechanical properties are not required.

The fillers predominantly perform the function of producing the BMC more economically in that fibre and resin volume is replaced by cheaper fillers. Depending on the desired properties, for example increased flameproofing or low shrinkage, additives are added. Thus, for example magnesium oxide increases the plasticity and kaolin increases the acid resistance.

Of course, the highest temperatures occur in the lighting unit. To date, the reflectors have therefore been produced either from sheet metal, from thermosetting plastics, such as BMC, or from metallized, injection-moulded amorphous high-Tg thermoplastics (PEI, PSU, PES). The high tolerance requirements coupled with the surface quality of the injection moulded parts which is required for metallization have been met to date mainly by filler-free amorphous high-Tg thermoplastics or coated thermosetting plastics.

An example of one of said high-Tg thermoplastics is the polyether sulphone ULTRASON E® from BASF Ludwigshafen, Germany (having an iridescence temperature of 212° C.), as described in the journal cited below. In the course of the progressive reduction of complexity, increasing integration of headlamp components to give highly developed lighting systems which are expected to permit higher material requirements is taking place at present (J. Queisser, M. Geprägs, R. Blum and G. Ickes, Trends bei Automobilscheinwerfern [Trends in automobile headlamps], Kunststoffe [Plastics] March 2002, Hanser Verlag, Munich).

The prior art moreover discloses compositions which comprise a fibrillar, inorganic filler (cf. EP 0 863 180) and an additional particulate inorganic filler (EP 1 312 647 or EP 0 585 056) or which comprise only a particulate, inorganic filler (EP 0 913 421). A material for the production of street light reflectors is known by the name MINLON® (E.I. du Pont de Nemours & Co., Wilmington, USA). Said product is the semicrystalline Nylon 66 (PA 66), which also comprises 36-40% of classical minerals in addition to a heat stabilizer. However, from the point of view of the surface quality, this material appears unsuitable, at least for vehicle lights. Here too, the considerable lengthening of the cycle times during injection moulding with such compositions compared with amorphous polymers is regarded as a further disadvantage.

A further requirement relates to the surface quality of the (generally curved) plastic surface to be coated. Especially in the case of reflectors, in which luminous efficiency is essential, a very smooth, highly glossy surface which is as homogeneous as possible must be provided for coating. Plastics which have poor flow or solidify too early or an addition of fillers often lead in the injection mould to a rough, matt or irregular impression, measured by the extremely high requirements of a mirror-smooth surface, even if the corresponding surface of the shaping mould is polished to a high gloss.

The prior art discloses further compositions without fillers. However, these likewise achieve only inadequate Tg values of less than 175° C. (cf. for example EP 0 313 436, EP 0 553 581 and U.S. Pat. No. 4,898,896). This category of polymers which are inadequate for the planned use also includes polyarylamides such as IXEF® 2057 (Solvay Advanced Polymers), polyarylates, polybutylene terephthalate (PBT, for example, ARNITE® TV4 220 from DSM).

The transparent, colourless and amorphous homopolyamides disclosed in the European patent EP 0 725 101 B2 have a glass transition temperature of about 157° C. and are at any rate suitable for the production of subreflectors, but unsuitable for the production of light-reflecting components which are exposed to operating temperatures of at least 200° C.

U.S. Pat. No. 6,355,723 B1 discloses injection moulded reflectors comprising amorphous thermoplastics, such as polyetherimides, polyaryl ethers, polyether sulphones, polysulphones, polycarbonates, polyestercarbonates, polyarylates, polyamides, polyesters and single-phase mixtures of said thermoplastics. These reflectors can be provided directly with a metal layer and have a glass transition temperature (Tg) of at least 170° C. to 200° C. In order to be able easily to detect any surface defects before the metallization of the reflector surface by means of visual inspection and to suppress undesired light effects due to unmetallized parts of the reflectors, all these reflectors are coloured black by admixing dyes.

However, owing to their excessively high coefficients of expansion, the polycarbonates or copolycarbonates previously described in the prior art have the disadvantage that they may have only limited suitability or even be unsuitable for use as a metallized component in, for example, high temperature applications as a reflector.

Polymer materials having very good optical and thermal properties are required for the use of flexible substrates for display applications, for example LCD or OLED displays. Thus, a sufficiently high glass transition temperature of the material is required for the production of the thin film transistor (TFT) elements on the substrates, for example by the a-Si:H method. Polyethylene naphthalate (PEN) has a low coefficient of thermal expansion but has only a low glass transition temperature of 120° C. and appears birefringent. Polyarylates (PAR) have a high glass transition temperature (215° C.) and an optically isotropic appearance but are very expensive materials. This also applies to polyether sulphone (PES, Tg=220° C.). Polyimides have the highest glass transition temperature (360° C.) in addition to very low coefficients of thermal expansion but seem orange to brown in optical appearance. The costs for these materials are likewise very high. For applications in display technology, very good optical properties, such as high transparency without birefringence, are additionally required. A polymer material which has very good transparency in combination with isotropic optical appearance at acceptable costs and at simultaneously high glass transition temperature and low thermal expansion would be desirable for display technology.

It was therefore the object to develop aromatic (co) polycarbonates which have reduced coefficients of thermal expansion and are simultaneously distinguished by outstanding adhesion to metal and good thermal properties (in particular high Vicat or glass transition temperature) in combination with a good surface (which is suitable for direct coating with a metal layer without additional pretreatment step) and can be prepared with good heat distortion resistance comparable to that of materials disclosed in the prior art.

The novel compositions should moreover show improved flowability.

EMBODIMENTS OF THE INVENTION

An embodiment of the present invention is a compound of formula (I)

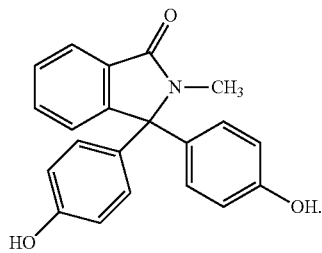
(I)

Yet another embodiment of the present invention is a process for preparing the compound of formula (I)

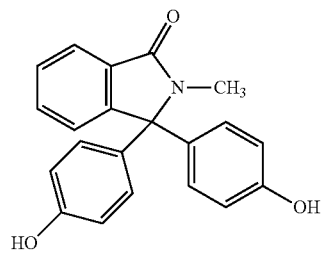
(I)

comprising reacting phenolphthalein with an aqueous methylamine solution in the presence of N-methylpyrrolidone.

Another embodiment of the present invention is the above process, further comprising isolating and purifying said compound of formula (I) by precipitating it in an aqueous solution comprising hydrochloric acid and subsequently dissolving said compound of formula (I) in sodium hydroxide solution.

Yet another embodiment of the present invention is a (co)polycarbonate comprising a bisphenol of formula (Ia) as a repeating monomer unit in said (co)polycarbonate

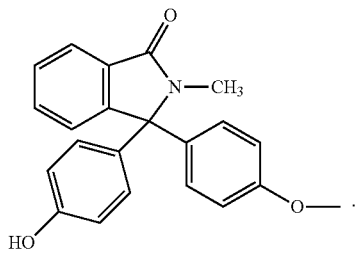
(Ia)

Another embodiment of the present invention is the above (co)polycarbonate, further comprising up to 95 mol %, based on the amount of diphenols used, of repeating monomer units based on one or more diphenols selected from diphenols of formula (II)

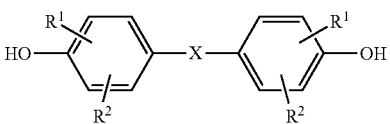
(II)

wherein
$R^1$ and $R^2$ are, independently of one another, hydrogen, $C_1$-$C_{18}$-alkyl, $C_1$-$C_{18}$-alkoxy, halogen, and optionally substituted aryl or aralkyl, and
X is a single bond, —$SO_2$—, —CO—, —O—, —S—, $C_1$- to $C_6$-alkylene, $C_2$- to $C_5$-alkylidene, or $C_5$- to $C_6$-cycloalkylidene, wherein said $C_1$- to $C_6$-alkylene, $C_2$- to $C_5$-alkylidene, and $C_5$- to $C_6$-cycloalkylidene is optionally substituted by $C_1$- to $C_6$-alkyl, or $C_6$-$C_{12}$-arylene, which is optionally condensed with further aromatic rings containing heteroatoms, and/or
diphenols of formula (IV), wherein said diphenols of formula (IV) is an isomer mixture of diphenols of formulae (IVa) and (IVb)

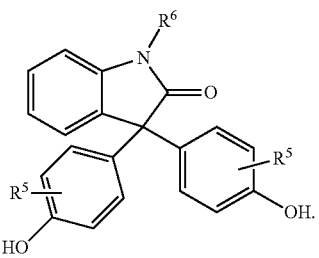
(IVa)

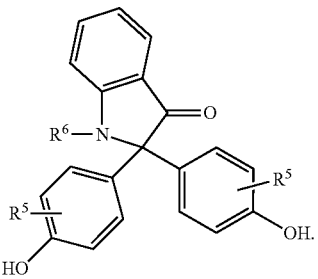
(IVb)

wherein
$R^5$ is, independently of one another, hydrogen or $C_1$-$C_{10}$ alkyl, and
$R^6$ is $C_1$-$C_{10}$ alkyl or optionally substituted phenyl or benzyl.

Another embodiment of the present invention is the above (co)polycarbonate, comprising from 20 to 100 mol % of repeating monomer units based on the diphenol of formula (I) and from 80 to 0 mol %, in each case based on the amount of diphenols used, of repeating monomer units based on the diphenols of formula (II) and/or (IV).

Another embodiment of the present invention is the above (co)polycarbonate, wherein said diphenols of formula (II) are selected from the group consisting of bisphenol A, 4,4'-dihydroxybiphenyl, 2,2-bis(3-methyl-4-hydroxyphenyl)propane, and bisphenol TMC.

Another embodiment of the present invention is the above (co)polycarbonate, wherein said (co)polycarbonate further comprises one or more additives selected from the group consisting of heat stabilizers, demoulding agents, UV absorbers, and fillers.

Another embodiment is a blend comprising one or more of the above (co)polycarbonates and one or more thermoplastic polymers.

Yet another embodiment of the present invention is a shaped article obtained from the above (co)polycarbonate.

Another embodiment of the present invention is the above shaped article, wherein said shaped article is produced via injection moulding or an extrusion process.

Yet another embodiment of the present invention is a multilayer product comprising a substrate layer comprising a further layer at least on one side, wherein said substrate layer comprises the above polycarbonate.

Another embodiment of the present invention is the above multilayer product, wherein said further layer on said substrate layer is a metal layer.

Another embodiment of the present invention is the above multilayer product, further comprising a protective layer applied to said metal layer.

Yet another embodiment of the present invention is a process for producing the above multilayer product, comprising the step of applying said protective layer in a PECVD or plasma polymerization process.

Another embodiment of the present invention is the above process, comprising the step of applying said protective layer in a PECVD or plasma polymerization process from one or more readily volatile components selected from the group consisting of hexamethyldisiloxane (HMDSO), hexamethyldisilazane (HMDS), tetramethyldisiloxane, decamethylcyclopentasiloxane, octamethylcyclotetrasiloxane, and trimethoxymethylsilane.

Yet another embodiment of the present invention is a process for preparing the above (co)polycarbonate comprising the step of using a compound of formula (I) as bisphenol in an interfacial process or a melt transesterification process.

BRIEF DESCRIPTION OF THE DRAWINGS

FIG. 1—Synthesis of the monomer building block according to the invention

DESCRIPTION OF THE INVENTION

In the context of this application, polycarbonate compositions (or blends) are understood as meaning mixtures of two or more polycarbonates which may optionally be provided with additives (further component).

Surprisingly, it has now been found that a copolycarbonate containing the structural unit of the formula (I) has lower coefficients of thermal expansion in combination with constant thermal properties (Vicat temperature) and mechanical and optical properties:

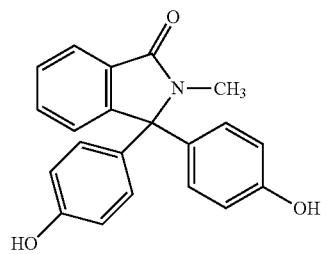

(I)

The invention accordingly relates to a process for the preparation of the phthalimide of the formula (I), comprising the reaction of phenolphthalein with an aqueous methylamine solution in the presence of N-methylpyrrolidone.

A 20 to 80% strength by weight, preferably 30 to 60% strength by weight, particularly preferably 35 to 45% strength by weight methylamine solution, preferably an aqueous solution, in a 3.5- to 4.5-fold molar excess of phenolphthalein in solution, preferably an N-methylpyrrolidone and water mixture, is preferably reacted. 2 kg of N-methylpyrrolidone and 2 kg of water are preferably used as a solvent mixture per 4 mol of phenolphthalein.

The N-methylpyrrolidone is preferably initially introduced at 40 to 60° C., particularly preferably 45 to 55° C., very particularly preferably at 50° C. and the phenolphthalein reactant is added. After a homogeneous solution has been obtained, the remaining water of the solvent mixture and the methylamine solution are added as a further reactant. The reaction preferably takes place in a temperature range from 65 to 95° C., preferably 75 to 90° C. and particularly preferably at 80 to 88° C.

The isolation and purification of the product are effected by precipitation in an aqueous solution containing hydrochloric acid, preferably 37% strength, and subsequent dissolution in sodium hydroxide solution by known methods. The cycle of isolation and purification is carried out several times in succession, preferably 1-3 times.

The invention furthermore relates to the preparation and use of a thermoplastic polymer moulding material containing the monomer building block (I) for the production of optionally metallically coated components suitable for operating temperatures of at least 160° C., preferably 180° C., particularly preferably 200° C., in particular LED applications and film substrates, light-reflecting components, and corresponding light-reflecting components which are metallically coated or are to be metallically coated, such as reflectors or subreflectors, and the corresponding components obtained therefrom.

The invention furthermore relates to the preparation of a polycarbonate with the use of the diphenol according to the invention and to the corresponding preparation processes, These polycarbonates are obtained by subjecting the bisphenol building block according to the invention to condensation with optionally further bisphenol building blocks in the interfacial process or the melt transesterification process to give relatively high molecular weight copolycarbonates.

The (co)polycarbonates according to the invention are based on bisphenols of the general formula (Ia) as a repeating monomer unit:

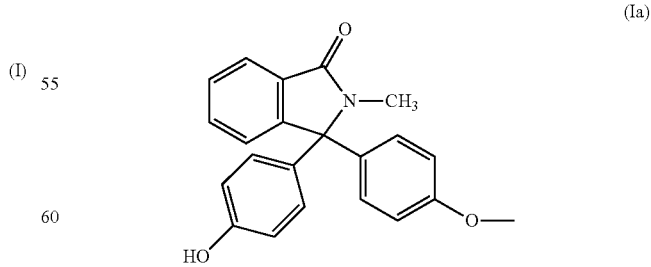

(Ia)

In the case of (co)polycarbonates, it is possible, in addition to one or more diphenols of the formula (I), for bisphenols of the formula (II) to be present as a further monomer unit:

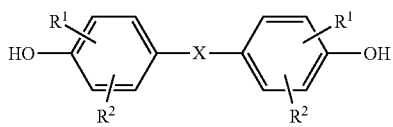

(II)

in which
R1 and R2, independently of one another, represent H, C1-C18-alkyl-, C1-C18-alkoxy, halogen, such as Cl or Br, or represent in each case optionally substituted aryl or aralkyl, preferably H or C1-C12-alkyl, particularly preferably H or C1-C8-alkyl and very particularly preferably H or methyl, and X represents a single bond, —SO$_2$—, —CO—, —O—, —S—, C$_1$- to C$_6$-alkylene, C$_2$- to C$_5$-alkylidene or C$_5$- to C$_6$-cycloalkylidene, which may be substituted by C$_1$- to C$_6$-alkyl, preferably methyl or ethyl, or furthermore represents C$_6$- to C$_{12}$-arylene, which may optionally be condensed with further aromatic rings containing heteroatoms.

Preferably, X represents a single bond, C1 to C5-alkylene, C2 to C5-alkylidene, C5 to C6-cycloalkylidene, —O—, —SO—, —CO—, —S—, —SO2- or one a radical of the formula (III)

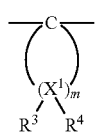

(III)

in which
R$^3$ and R$^4$, individually selectable for each X$^1$, denote, independently of one another, hydrogen or C$_1$ to C$_6$-alkyl, preferably hydrogen, methyl or ethyl, and
X$^1$ denotes carbon and
m denotes an integer from 4 to 7, preferably 4 or 5, with the proviso that R3 and R4 are simultaneously alkyl on at least one atom X$^1$.

For the preparation of the copolycarbonates according to the invention, bisphenol A, 2,2-bis(3-methyl-4-hydroxyphenyl)propane (dimethyl bisphenol A), 1,1-bis(4-hydroxyphenyl)-3,3,5-trimethylcyclohexane (bisphenol TMC) and 1,1-bis(3-methyl-4-hydroxyphenyl)-3,3,5-trimethylcyclohexane (dimethyl TMC) is preferably used as a diphenol derived from formula (II).

Diphenols which are suitable for the preparation of the copolycarbonates to be used according to the invention and which are based on the structural unit according to formula (II) are, for example, hydroquinone, resorcinol, bis(hydroxyphenyl)alkanes, bis(hydroxyphenyl) sulphides, bis(hydroxyphenyl)ethers, bis(hydroxyphenyl) ketones, bis(hydroxyphenyl) sulphones, bis(hydroxyphenyl) sulphoxides, α,α'-bis(hydroxyphenyl)diisopropylbenzenes, and the compounds thereof which are alkylated, alkylated on the nucleus and halogenated on the nucleus.

Preferred diphenols are 4,4'-dihydroxybiphenyl, 2,2-bis(4-hydroxyphenyl)-1-phenylpropane, 1,1-bis(4-hydroxyphenyl)phenylethane, 2,2-bis(4-hydroxyphenyl)propane, 2,2-bis(3-methyl, 4-hydroxyphenyl)propane, 2,4-bis(4-hydroxyphenyl)-2-methylbutane, 1,3-bis[2-(4-hydroxyphenyl)-2-propyl]benzene (bisphenol M), 2,2-bis(3-methyl-4-hydroxyphenyl)propane, bis(3,5-dimethyl-4-hydroxyphenyl)methane, 2,2-bis(3,5-dimethyl-4-hydroxyphenyl)propane, bis(3,5-dimethyl-4-hydroxyphenyl) sulphone, 2,4-bis(3,5-dimethyl-4-hydroxyphenyl)-2-methylbutane, 1,3-bis[2-(3,5-dimethyl-4-hydroxyphenyl)-2-propyl]benzene, 1,1-bis(4-hydroxyphenyl)-3,3,5-trimethylcyclohexane, 2,2-bis(4-hydroxyphenyl)-1-phenyl-1H-indol-3-one, 3,3-bis(4-hydroxyphenyl)-1-phenyl-1H-indol-2-one.

Furthermore, bisphenols of the general formulae (IVa) and (IVb) (isomer mixture) (also referred to below as bisphenols of the formula (IV)) can be used as a further diphenol compound.

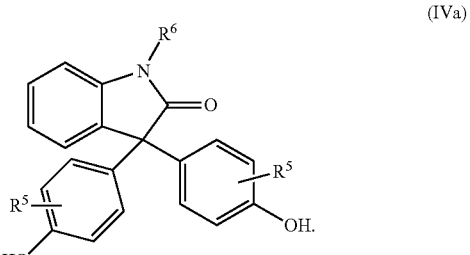

(IVa)

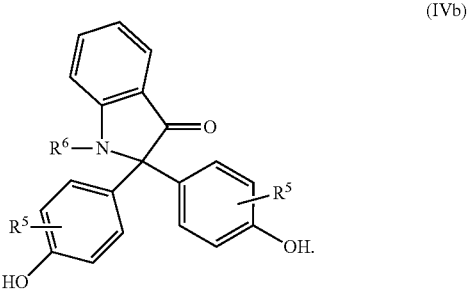

(IVb)

in which:
R$^5$ independently of one another, represents hydrogen or C$_1$-C$_{10}$ alkyl, preferably hydrogen or C$_1$-C$_6$ alkyl, particularly preferably hydrogen or C$_1$-C$_4$ alkyl, very particularly preferably hydrogen or methyl
R$^6$ represents C$_1$-C$_{10}$ alkyl, preferably C$_1$-C$_6$ alkyl, particularly preferably C$_1$-C$_4$ alkyl, in each case optionally substituted phenyl or benzyl, in particular methyl, phenyl or benzyl, the radicals mentioned in the case of R$^1$ being preferred as substituents for phenyl and benzyl.

In the context of the present invention, alkyl is in each case linear or branched,
R$^6$ particularly preferably represents phenyl optionally substituted by the radicals mentioned in R$^5$, represented by the formulae (IVc) and (IVd) (isomer mixture),

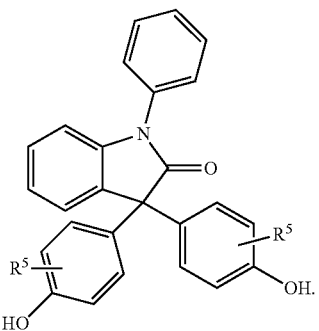

(IVc)

-continued

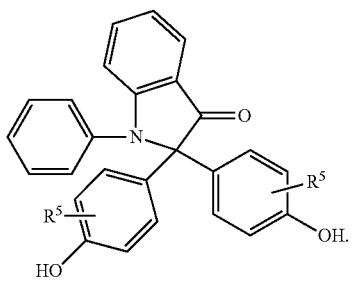
(IVd)

in which
$R^5$ has the abovementioned meaning.

The bisphenol of the formulae (IVe) and (IVf) (isomer mixture) is very particularly preferred.

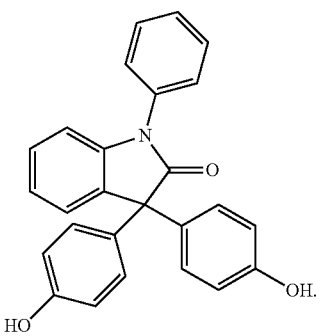
(IVe)

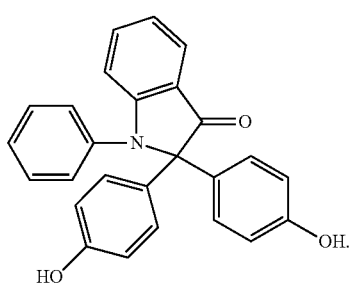
(IVf)

Particularly preferred diphenols are 2,2-bis(4-hydroxyphenyl)propane (bisphenol A) and 2,2-bis(3-methyl-4-hydroxyphenyl)propane (dimethyl bisphenol A) or bisphenol TMC and the bisphenols of the formula (IV).

Copolycarbonates obtained from the bisphenol (I) according to the invention and bisphenol A or bisphenol TMC or dimethyl bisphenol A are particularly preferred.

These and further suitable diphenols are commercially available and are described, for example, in "H. Schnell, Chemistry and Physics of Polycarbonates, Interscience Publishers, New York 1964, page 28 et seq.; page 102 et seq.", and in "D. G. Legrand, J. T. Bendler, Handbook of Polycarbonate Science and Technology, Marcel Dekker New York 2000, page 72 et seq.".

The bisphenol of the formula (I) can be used either alone or as a mixture with one or more bisphenols of the formula (II) and/or (IV); in the context of the present invention, polycarbonates are to be understood as meaning both homopolycarbonates and copolycarbonates.

In addition to a diphenol selected from compounds of the formula (I), copolycarbonates generally contain up to 95 mol %, preferably up to 80 mol %, particularly preferably up to 70 mol %, of at least one further diphenol selected from compounds of the formula (II) and/or (IV) (based on the sum of the moles of diphenols used). Preferably, the copolycarbonates contain, as the lower limit, at least 5 mol %, in particular 10 mol % (based on the sum of the moles of diphenols used), selected from compounds of the formula (II) and/or (IV). Particularly preferred copolycarbonates contain 40-60, in particular 45-55 mol % of diphenol of the formula (I) and 60-40, in particular 45-55 mol % of diphenol(s) of the formula (II) and/or (IV) (based on the sum of the moles of diphenols used).

The thermoplastic polycarbonates and copolycarbonates according to the invention generally have average molecular weights (weight average Mw, determined by gel permeation chromatography GPC measurement with polycarbonate calibration) of 2000 g/mol to 200 000 g/mol, preferably 3000 g/mol to 150 000 g/mol, in particular 5000 g/mol to 100 000 g/mol, very particularly preferably 8000 g/mol to 80 000 g/mol, in particular 12 000 g/mol to 70 000 g/mol. Molecular weights can also be specified by the number average Mn, which are likewise determined by means of GPC after prior calibration to polycarbonate.

The invention furthermore relates to blends containing one or more (co)polycarbonates according to the invention and one or more thermoplastic polymers.

A preferably used thermoplastic polymer is at least one from the series consisting of polycarbonate, polyamide, polyester, in particular polybutyleneterephthalate and polyethyleneterephthalate, polylactide, polyether, thermoplastic polyurethane, polyacetal, fluorine polymer, in particular polyvinylidene fluoride, polyether sulphones, polyolefin, in particular polyethylene and polypropylene, polyimide, polyacrylate, in particular poly(methyl)methacrylate, polyphenylene oxide, polyphenylene sulphide, polyether ketone, polyaryl ether ketone, styrene polymers, in particular polystyrene, styrene copolymers, in particular styrene-acrylonitrile copolymer, acrylonitrile-butadiene-styrene block copolymers and polyvinyl chloride.

Polycarbonates are particularly preferred as a blend component.

The diphenols used, as well as all other chemicals and auxiliaries added to the synthesis, may be contaminated with the impurities originating from their own synthesis, handling and storage. However, it is desirable to work with raw materials which are as pure as possible.

In order to obtain high molecular polycarbonates by the interfacial process, the alkali metal salts of diphenols are reacted with phosgene in the two-phase mixture. The molecular weight can be controlled by the amount of monophenols, which act as chain terminators, such as, for example phenol, tert.-butylphenol or cumylphenol, particularly preferably phenol, tert-butylphenol. In these reactions, virtually exclusively linear polymers form. This can be detected by end group analysis. By targeted use of so-called branching agents, as a rule polyhydroxylated compounds, branched polycarbonates are also obtained.

The amount of chain terminators to be used is 0.5 mol % to 10 mol %, preferably 1 mol % to 8 mol %, particularly preferably 2 mol % to 6 mol %, based on moles of diphenols used in each case. The addition of the chain terminators can be effected before, during or after the phosgenation, preferably as a solution in a solvent mixture comprising methylene chloride and chlorobenzene (8-15% strength by weight).

The polycarbonates or copolycarbonates may also be branched. For this purpose, certain small amounts, preferably amounts between 0.05 and 5 mol %, particularly preferably 0.1 to 3 mol %, very particularly preferably 0.1 to 2 mol %, based on the moles of diphenols used, of trifunctional compounds, such as, for example, isatinbiskresol (IBK) or phloroglucin, 4,6-dimethyl-2,4,6-tri(4-hydroxyphenyl)hept-2-ene; 4,6-dimethyl-2,4,6-tri(4-hydroxyphenyl)heptane; 1,3,5-tri(4-hydroxyphenyl)benzene; 1,1,1-tri(4-hydroxyphenyl)ethane (THPE); tri(4-hydroxyphenyl)phenylmethane; 2,2-bis[4,4-bis(4-hydroxyphenyl)cyclohexyl]propane; 2,4-bis(4-hydroxyphenylisopropyl)henol; 2,6-bis(2-hydroxy-5'-methylbenzyl)-4-methylphenol; 2-(4-hydroxyphenyl)-2-(2,4-dihydroxyphenyl)propane; hexa(4-(4-hydroxyphenylisopropyl)phenyl)ortho-terephthalic acid ester; tetra(4-hydroxyphenyl)methane; tetra(4-(4-hydroxyphenylisopropyl)phenoxy)methane; α,α,α,"-tris(4-hydroxyphenyl)-1,3,5-triisopropylbenzene; 2,4-dihydroxybenzoic acid; trimeric acid; cyanuric chloride; 3,3-bis(3-methyl-4-hydroxyphenyl)-2-oxo-2,3-dihydroindole; 1,4-bis(4',4"-dihydroxy-triphenyl)methyl)benzene and in particular 1,1,1-tri(4-hydroxyphenyl)ethane and bis(3-methyl-4-hydroxyphenyl)-2-oxo-2,3-dihydroindole are used as so-called branching agents. Isatinbiskresol as well as 1,1,1-tri(4-hydroxyphenyl)ethane and bis(3-methyl-4-hydroxyphenyl)-2-oxo-2,3-dihydroindole are preferably used as branching agents.

The use of these branching agents results in branched structures. The resulting long-chain branching leads to rheological properties of the polycarbonates obtained which manifests itself in a structural viscosity in comparison with linear types.

The present invention furthermore relates to a process for the preparation of the polycarbonates and copolycarbonates according to the invention, characterized in that bisphenols and possibly branching agents are dissolved in aqueous alkaline solution and reacted with a carbonate source, such as phosgene, optionally dissolved in a solvent, in a two-phase mixture comprising an aqueous alkaline solution, an organic solvent and a catalyst, preferably an amine compound. The reaction procedure can also be effected in a plurality of stages. Such processes for the preparation of polycarbonate are known in principle as interfacial processes, for example from H. Schnell, Chemistry and Physics of Polycarbonates, Polymer Reviews, Vol. 9, Interscience Publishers, New York 1964 page 33 et seq., and on Polymer Reviews, Vol. 10, "Condensation Polymers by Interfacial and Solution Methods", Paul W. Morgan, Interscience Publishers, New York 1965, chapter VIII, page 325, and the underlying conditions are therefore familiar to the person skilled in the art.

The concentration of the bisphenols in the aqueous alkali solution is 2 to 25% by weight, preferably 2 to 20% by weight, particularly preferably 2 to 18% by weight and very particularly preferably 3 to 15% by weight. The aqueous alkaline solution consists of water, in which hydroxides of alkali metals or alkaline earth metals are dissolved. Sodium and potassium hydroxide are preferred.

With the use of phosgene as a carbonate source, the volume ratio of aqueous alkaline solution to organic solvent is 5:95 to 95:5, preferably 20:80 to 80:20, particularly preferably 30:70 to 70:30 and very particularly preferably 40:60 to 60:40. The molar ratio of bisphenol to phosgene is less than 1:10, preferably less than 1:6, particularly preferably less than 1:4 and very particularly preferably less than 1:3. The concentration of the branched polycarbonates and copolycarbonates according to the invention in the organic phase is 1.0 to 25% by weight, preferably 2 to 20% by weight, particularly preferably 2 to 18% by weight and very particularly preferably 3 to 15% by weight.

The concentration of the amine compound, based on the amount of bisphenol used, is 0.1 to 10 mol %, preferably 0.2 to 8 mol %, particularly preferably 0.3 to 6 mol % and very particularly preferably 0.4 to 5 mol %.

Bisphenols are to be understood as meaning the abovementioned diphenols, with proportions of the abovementioned branching agents. The carbonate source is phosgene, diphosgene or triphosgene, preferably phosgene. Where phosgene is used, it is optionally possible to dispense with a solvent and to pass the phosgene directly into the reaction mixture.

Tertiary amines, such as triethylamine or N-alkylpiperidines, may be used as catalyst. Suitable catalysts are trialkylamines and 4-(dimethylamino)pyridine. Triethylamine, tripropylamine, triisopropylamine, tributylamine, triisobutylamine, N-methylpiperidine, N-ethylpiperidine and N-propylpiperidine are particularly suitable.

Halogenated hydrocarbons, such as methylene chloride and/or chlorobenzene, dichlorobenzene, trichlorobenzene or mixtures thereof, or aromatic hydrocarbons, such as, for example, toluene or xylenes, are suitable as an organic solvent.

The reaction temperature may be −5° C. to 100° C., preferably 0° C. to 80° C., particularly preferably 10° C. to 70° C. and very particularly preferably 10° C. to 60° C.

Alternatively, the polycarbonates according to the invention may also be prepared by the melt transesterification process. The melt transesterification process is described, for example, in Encyclopaedia of Polymer Science, Vol. 10 (1969), Chemistry and Physics of Polycarbonates, Polymer Reviews, H. Schnell, Vol, 9, John Wiley and Sons, Inc. (1964), and DE-C 10 31 512.

In the melt transesterification process, the aromatic dihydroxy compounds already described in the case of an interfacial process are transesterified with carbonic acid diesters with the aid of suitable catalysts and optionally further additives in the melt.

In the context of the invention, carbonic acid diesters are those of the formulae (6) and (7)

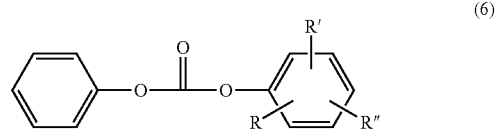

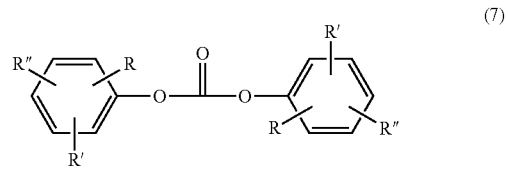

in which
R, R' and R", independently of one another, may represent H, optionally branched $C_1$-$C_{34}$-alkyl/cycloalkyl, $C_7$-$C_{34}$-alkaryl or $C_6$-$C_{34}$-aryl,
for example
diphenyl carbonate, butylphenyl phenyl carbonate, dibutylphenyl carbonate, isobutylphenyl phenyl carbonate, diisobutylphenyl carbonate, tert-butylphenyl phenyl carbonate, di-tert-butylphenyl carbonate, n-pentylphenyl phenyl carbonate, di(n-pentylphenyl) carbonate, n-hexylphenyl phenyl carbonate, di(n-hexylphenyl) carbonate, cyclohexylphenyl phenyl carbonate, dicyclohexylphenyl carbonate, phenylphenol phenyl carbonate, diphenylphenol carbonate, isooctylphenyl phenyl carbonate, diisooctylphenyl carbonate, n-nonylphenyl phenyl carbonate, di(n-nonylphenyl) carbonate, cumylphenyl phenyl carbonate, dicumylphenyl carbonate, naphthylphenyl phenyl carbonate, dinaphthylphenyl carbonate, di-tert-butylphenyl phenyl carbonate, di(di-tert-butylphenyl) carbonate, dicumylphenyl phenyl carbonate, di(dicumylphenyl) carbonate, 4-phenoxyphenyl phenyl carbonate, di(4-phenoxyphenyl) carbonate, 3-pentadecylphenyl phenyl carbonate, di(3-pentadecylphenyl) carbonate, tritylphenyl phenyl carbonate, ditritylphenyl carbonate,
preferably diphenyl carbonate, tert-butylphenyl phenyl carbonate, di-tert-butylphenyl carbonate, phenylphenol phenyl carbonate, diphenylphenol carbonate, cumylphenyl phenyl carbonate, dicumylphenyl carbonate,
particularly preferably diphenyl carbonate.

It is also possible to use mixtures of said carbonic acid diesters.

The proportion of carbonic acid ester is 100 to 130 mol %, preferably 103 to 120 mol %, particularly preferably 103 to 109 mol %, based on the dihydroxy compound.

In the context of the invention, basic catalysts, such as, for example, alkali metal and alkaline earth metal hydroxides and oxides, but also ammonium or phosphonium salts, referred to below as onium salts, are used as catalysts in the melt transesterification process, as described in the stated literature. Onium salts, in particular phosphonium salts, are preferably used here. Phosphonium salts in the context of the invention are those of the formula (IV)

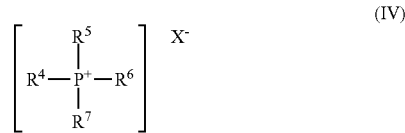

in which
$R^{4-7}$ may be the same or different $C_1$-$C_{10}$-alkyls, $C_6$-$C_{10}$-aryls, $C_7$-$C_{10}$-aralkyls or $C_5$-$C_6$-cycloalkyls, preferably methyl, or $C_6$-$C_{14}$-aryls, particularly preferably methyl or phenyl, and $X^-$ may be an anion such as hydroxide, sulphate, hydrogen sulphate, bicarbonate, carbonate, a halide, preferably chloride, or an alkoholate of the formula OR, in which R may be $C_6$-$C_{14}$-aryl or $C_7$-$C_{12}$-aralkyl. Preferred catalysts are
tetraphenylphosphonium chloride, tetraphenylphosphonium hydroxide, tetraphenyl-phosphonium phenolate, particularly preferably tetraphenylphosphonium phenolate.

The catalysts are preferably used in amounts of $10^{-8}$ to $10^{-3}$ mol, based on one mole of bisphenol, particularly preferably in amounts of $10^{-7}$ to $10^{-4}$ mol.

Further catalysts may be used alone or optionally in addition to the onium salt in order to increase the rate of the polymerization. These include salts of alkali metals and alkaline earth metals such as hydroxides, alkoxides and aryl oxides of lithium, sodium and potassium, preferably hydroxide, alkoxide or aryl oxide salts of sodium. Sodium hydroxide and sodium phenolate are most preferred. The amounts of the cocatalyst may be in the range from 1 to 200 ppb, preferably 5 to 150 ppb and most preferably 10 to 125 ppb, calculated in each case as sodium.

The transesterification reaction of the aromatic dihydroxy compound and of the carbonic acid diester in the melt is preferably carried out in two stages. In the first stage, the melting of the aromatic dihydroxy compound and of the carbonic acid diester takes place at temperatures of 80 to 250° C., preferably 100 to 230° C., particularly preferably 120 to 190° C., under atmospheric pressure in 0 to 5 hours, preferably 0.25 to 3 hours. After addition of the catalyst, the oligocarbonate is prepared from the aromatic dihydroxy compound and the carbonic acid diester by distilling off the monophenol by applying a vacuum (up to 2 mm/Hg) and increasing the temperature (up to 260° C.). The main amount of vapours from the process occurs here. The oligocarbonate thus prepared has a weight average molar mass $M_W$ (determined by measurement of the relative solution viscosity in dichloromethane or in mixtures of equal amounts by weight of phenol/o-dichlorobenzene, calibrated by light scattering) in the range from 2000 g/mol to 18 000 g/mol, preferably from 4000 g/mol to 15 000 g/mol.

In the second stage, the polycarbonate is prepared in the polycondensation by a further increase in the temperature to 250 to 320° C., preferably 270 to 295° C., and a pressure of <2 mm/Hg. The remainder of vapours is removed from the process in this case.

The catalysts can also be used in combination (two or more) with one another.

With the use of alkali metal/alkaline earth metal catalysts, it may be advantageous to add the alkali metal/alkaline earth metal catalysts at a later time (for example after the oligocarbonate synthesis, during the polycondensation in the second stage).

The reaction of the aromatic dihydroxy compound and of the carbonic acid diester to give the polycarbonate can be carried out batchwise or preferably continuously in the process according to the invention, for example in stirred vessels, thin film evaporators, falling-film evaporators, stirred vessel cascades, extruders, kneaders, simple disc reactors and high-viscosity disc reactors.

Analogously to the interfacial process, branched poly- or copolycarbonates can be prepared by using polyfunctional compounds.

Embodiments which make use of the parameters, compounds, definitions and explanations mentioned below as being preferred, particularly preferred or very particularly preferred, etc. are preferred, particularly preferred or very particularly preferred.

The general definitions, parameters, compounds and explanations mentioned in the description or mentioned in preferred ranges can, however, also be arbitrarily combined with one another, i.e. between the respective ranges and preferred ranges.

The polycarbonates and copolycarbonates according to the invention can be worked up in a known manner and processed to give any mouldings, for example by extrusion, injection moulding or extrusion blow moulding.

Yet other aromatic polycarbonates and/or other aromatic polyester carbonates and/or other aromatic polyesters can be mixed in a known manner with the polycarbonates and copolycarbonates according to the invention, for example by compounding.

The composition may contain further commercially available polymer additives, such as flame-retarding agents, flame-proofing synergistic agents, antidrip agents (for example compounds of the classes of substances consisting of the fluorinated polyolefins, the silicones and aramid fibres), lubricants and release agents (for example pentaerythrityltetrastearate), nucleating agents, stabilizers, antistatic agents (for example conductive carbon blacks, carbon fibres, carbon nanotubes and organic antistatic agents such as polyalkylene ethers, alkyl sulphonates and polyamide-containing polymers), and colorants and pigments in those amounts which do not adversely affect the mechanical properties of the composition to such an extent that the target property profile (no fracture failure with splintering at −10° C.) is no longer fulfilled.

Preferred flame-retarding agents are sulphonic acid salts, such as potassium perfluorobutanesulphonic acid or potassium diphenyl sulphone sulphonate, brominated oligobisphenol, PTFE or PTFE compounds and phosphorus-containing flame-retarding agents, in particular selected from the groups consisting of the mono- and oligomeric phosphoric and phosphonic acid esters, phosphonate amines and phosphazenes, it also being possible to use mixtures or a plurality of components selected from one of these groups or different groups from these groups as flame-retarding agents. Other, preferably halogen-free phosphorus compounds not specifically mentioned here can also be used, alone or in any combination with other, preferably halogen-free phosphorus compounds. For example, the following are suitable as phosphorus compounds: tributyl phosphate, triphenyl phosphate, tricresyl phosphate, diphenyl cresyl phosphate, diphenyl octyl phosphate, diphenyl 2-ethylcresyl phosphate, tri(isopropylphenyl) phosphate, resorcinol-bridged di- or oligophosphate and bisphenol A-bridged di- or oligophosphate. The use of oligomeric phosphoric acid esters which are derived from bisphenol A is particularly preferred. Phosphorus compounds suitable as flame-retarding agents are known (cf. for example EP-A 0 363 608, EP-A 0 640 655) or can be prepared in an analogous manner by known methods (e.g. Ullmanns Enzyklopädie der technischen Chemie [Ullmann's Encyclopaedia of Industrial Chemistry], Vol. 18, page 301 et seq., 1979; Houben-Weyl, Methoden der organischen Chemie [Methods of Organic Chemistry], Vol. 12/1, page 43; Beilstein Vol. 6, page 177).

The addition of additives serves for lengthening the duration of use or the colour (stabilizers), simplifying the process (e.g. release agent, flow improver, antistatic agents) or adapting the polymer properties to certain loads (impact modifiers, such as rubbers; flame-retarding agents, colorants, glass fibres).

These additives can be added individually or in any desired mixtures or a plurality of different mixtures to the polymer melt, in particular directly during the isolation of the polymer or after melting of pellets in a so-called compounding step. The additives or the mixtures thereof can be added as solid, i.e. as powder, or as a melt to the polymer melt. Another method of metering is the use of masterbatches or mixtures of masterbatches of the additives or additive mixtures.

Suitable additives are described, for example, in "Additives for Plastics Handbook, John Murphy, Elsevier, Oxford 1999", in "Plastics Additives Handbook, Hans Zweifel, Hanser, Munich 2001" or in WO 99/55772, pages 15-25.

Suitable heat stabilizers are preferably tris(2,4-di-tert-butylphenyl) phosphite (Irgafos 168), tetrakis(2,4-di-tert-butylphenyl)[1,1-biphenyl]-4,4'-diyl bisphosphonite, triisoctyl phosphate, octadecyl-3-(3,5-di-tert-butyl-4-hydroxyphenyl)propionate (Irganox 1076 from BASF), bis(2,4-dicumylphenyl)pentaerythritol diphosphite (Doverphos S-9228-PC), bis(2,6-di-test-butyl-4-methylphenyl)pentaerythritol diphosphite (ADK STAB PEP-36) or triphenylphosphine. They are used alone or as a mixture (e.g. Irganox B900 from BASF or Doverphos S-9228-PC with Irganox B900 or Irganox 1076).

Suitable UV stabilizers are organic UV stabilizers. The UV stabilizers are preferably selected from the group consisting of benzotriazoles (e.g. Tinuvins from BASF), triazines CGX-06 from BASF), benzophenones (Uvinuls from BASF), cyanacrylates (Uvinuls from BASF), cinnamic acid esters and oxalanilides and mixtures of these UV stabilizers.

Examples of suitable UV absorbers are:
a) Malonic Esters of the Formula (I):

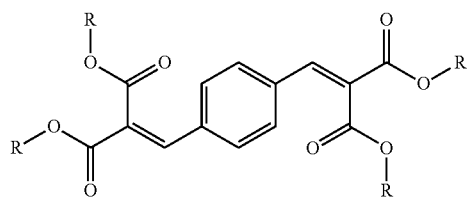

in which R denotes alkyl. Preferably, R represents C1-C6-alkyl, in particular C1-C4-alkyl and particularly preferably ethyl.

b) Benzotriazole Derivatives According to Formula (II):

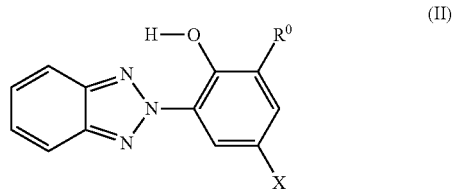

In formula (II), R° containing and X are identical or different and denote H or alkyl or alkylaryl.

Tinuvin® 329 where X=1,1,3,3-tetramethylbutyl and R°=H, Tinuvin® 350 where X=tert-butyl and R°=2-butyl and Tinuvin® 234 where X and R°=1,1-dimethyl-1-phenyl are preferred in this case.

c) Dimeric Benzotriazole Derivatives According to Formula (III):

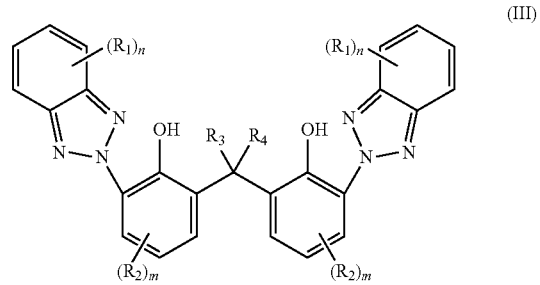

In formula (III), R1 and R2 are identical or different and denote H, halogen, C1-C10-alkyl, C5-C10-cycloalkyl, C7-C13-aralkyl, C6-C14-aryl, —OR5 or —(CO)—O—R5, where R5=H or C1-C4-alkyl.

In formula (III), R3 and R4 are likewise identical or different and denote H, C1-C4-alkyl, C5-C6-cycloalkyl, benzyl or C6-C14-aryl.

In formula (III) m denotes 1, 2 or 3 and n denotes 1, 2, 3 or 4.

Tinuvin® 360 where R1=R3=R4=H; n=4; R2=1,1,3,3-tetramethylbutyl; m=1 is preferred in this case.

d) Dimeric Benzotriazole Derivatives According to Formula (IV):

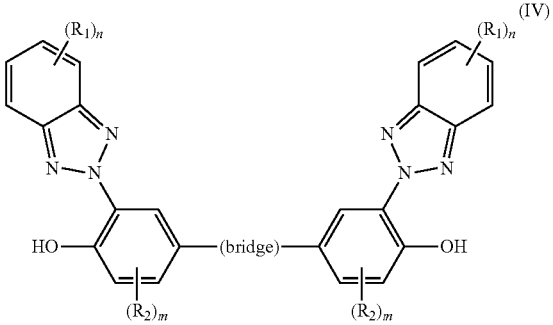

in which the bridge denotes

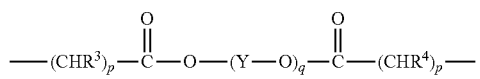

$R_1$, $R_2$, m and n have the meaning mentioned for formula (III), and in which p is an integer from 0 to 3, q is an integer from 1 to 10, Y is —CH2-CH2-, —(CH2)3-, —(CH2)4-, —(CH2)5-, —(CH2)6-, or CH(CH3)-CH2-ist and R3 and R4 have the meaning mentioned for formula (III).

Tinuvin® 840 where R1=H; n=4; R2=tert-butyl; m=1; R2 is attached in the ortho-position to the OH group; R3=R4=H; p=2; Y=—(CH2)5-; q=1 is preferred in this case.

e) Triazine Derivatives According to Formula (V):

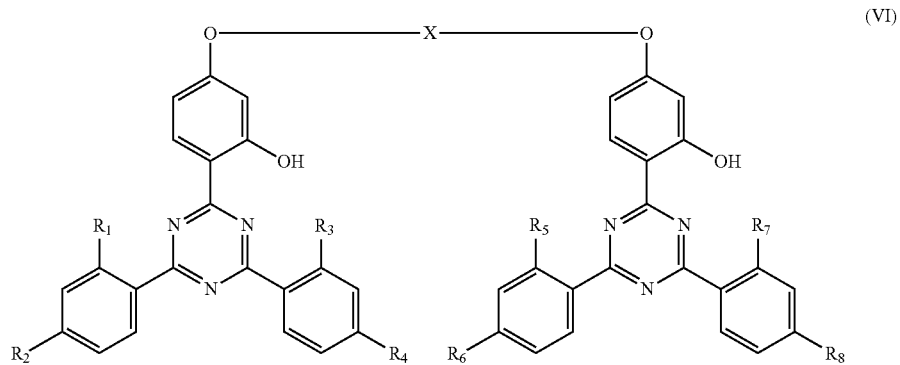

(V)

in which R1, R2, R3, R4 are identical or different and H, alkyl, aryl, CN or halogen and X is alkyl, preferably isooctyl.

Tinuvin® 1577 where R1=R2=R3=R4=H; X=hexyl, and Cyasorb® UV-1 164 where R1=R2=R3=R4=methyl; X is octyl is preferred in this case.

f) Triazine Derivatives of the Following Formula (Va):

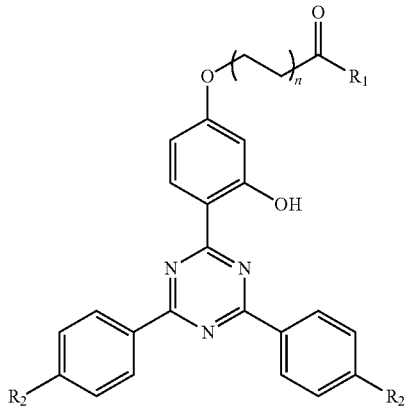

(Va)

in which R1 denotes C1 alkyl to C17-alkyl, R2 denotes H or C1-alkyl to C4-alkyl and n is 0 to 20.

g) Dimeric Triazine Derivatives of the Formula (VI):

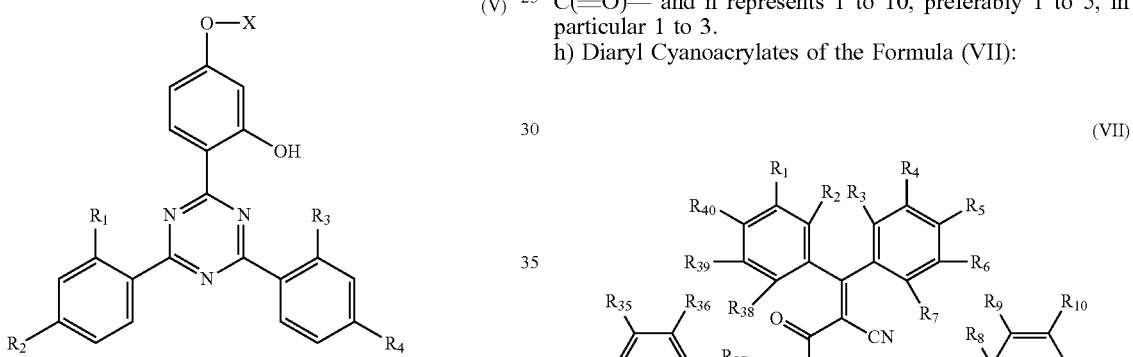

(VI)

in which R1, R2, R3, R4, R5, R6, R7, R8 may be identical or different and denote H, alkyl, CN or halogen and X is alkylidene, preferably methylidene, or —(CH2 CH2-O-)n-C(=O)— and n represents 1 to 10, preferably 1 to 5, in particular 1 to 3.

h) Diaryl Cyanoacrylates of the Formula (VII):

(VII)

in which R to R40 may be identical or different and denote H, alkyl, CN or halogen. Uvinul® 3030 where R1 to R40=H is preferred in this case.

Particularly preferred UV stabilizers for the moulding materials according to the invention are compounds from the group consisting of the benzotriazoles (b) and the dimeric benzotriazoles (c and d), the malonic esters (a) and the cyanoacrylates (h) and mixtures of these compounds.

The UV stabilizers are used in amounts of 0.01% by weight to 15.00% by weight, based on the moulding material, preferably in amounts of 0.05% by weight to 1.00% by weight, particularly preferably in amounts of 0.08% by weight to 0.5% by weight, and very particularly preferably in amounts of 0.1% by weight to 0.4% by weight, based on the total composition.

The release agents optionally added to the compositions according to the invention are preferably selected from the group consisting of pentaerythrityl tetrastearate, glyceryl monostearate, stearyl stearate and propoandiol stearate and mixtures thereof. The demoulding agents are used in amounts of 0.05% by weight to 2.00% by weight, based on the moulding material, preferably in amounts of 0.1% by weight to 1.0% by weight, particularly preferably in amounts of 0.15% by weight to 0.60% by weight and very particularly preferably in amounts of 0.2% by weight to 0.5% by weight, based on the total composition.

Furthermore, colorants, such as organic dyes or pigments or inorganic pigments, carbon black, IR absorbers, may be added individually, as a mixture or in combination with stabilizers, glass fibres, (hollow) glass spheres, inorganic fillers and organic or inorganic scattering pigments.

The invention also relates to processes for the preparation of the moulding materials and the use of the moulding materials for the production of mouldings.

The moulding materials according to the invention can be used for the production of mouldings of any kind. These can be produced, for example, by injection moulding, extrusion and blow moulding processes. A further form of processing is the production of mouldings by thermoforming from previously produced sheets or films.

The (co)polycarbonates and (co)polycarbonate compositions according to the invention can be processed in a customary manner on customary machines, for example on extruders or injection moulding machines, to give any desired moulding or shaped articles or to give films and film laminates or sheets or bottles.

The compounding of the individual constituents can be effected in a known manner, either successively or simultaneously.

The (co)polycarbonates thus obtainable can be used for the production of extrudates (sheets, films and laminates thereof; e.g. for card applications or film substrates for displays, such as LCDs and tubes) and mouldings (bottles), in particular those for use in the transparent area, particularly in the area of optical applications, such as, for example, sheets, multi-skin sheets, glazing, diffuser screens or lenses, lamp covers, plastic lenses, waveguide elements and LED applications. Furthermore, they can be used for the production of articles for the E/E and IT sector.

Furthermore, the invention relates to injection moulded bodies consisting of the substrate material according to the invention and a metal layer, preferably an aluminium layer, preferably in a thickness of 20-500 nm, particularly preferably in a thickness of 40-300 nm.

The metal layer is applied to the thermoplastic, for example, with the aid of Electro-Coating Deposition (ECD), Physical Vapour Deposition (PVD) or Chemical Vapour Deposition (CVD) or a suitable combination of these methods. Methods for the metallization of polymer materials are known in the literature.

In a particular embodiment, a protective layer, for example for corrosion protection, is also applied to the metal layer. The corrosion-reducing protective layer can be applied in a PECVD (plasma enhanced chemical vapour deposition) or plasma polymerization process. Here, low-boiling precursors, mainly based on siloxane, are evaporated in a plasma and activated thereby so that they can form a film. Typical substances here are hexamethyldisiloxane (HMDSO), hexamethyldisilazane (HMDS), tetramethyldisiloxane, decamethylcyclopentasiloxane, octamethylcyclotetrasiloxane and trimethoxymethylsilane. HMDSO is particularly preferred.

In a further particular embodiment, the substrate can be subjected, before the metallization, to a suitable pretreatment such as, for example, a plasma pretreatment, with the aim of activating or cleaning the substrate surface.

The (co)polycarbonate compositions are used in particular for the production of compounds, blends and components in which optical, thermal and mechanical properties are utilized, such as, for example, housings, articles in the E/E sector, such as plugs, switches, boards, lamp holders, lamp covers, the automotive sector, such as lamp bezels and lamp covers, glazing, lenses, collimators, light emitting diodes or diffuser sheets for displays and other applications.

The polycarbonates and copolycarbonates according to the invention, optionally as a mixture of other thermoplastics, such as, for example graft polymers based on acrylonitrile/butadiene/styrene or graft copolymers based on acrylate rubber (cf. for example the graft polymers described in EP-A 640 655) and/or customary additives, can be processed to give any desired mouldings/extrudates which are used wherever known polycarbonates, polyester carbonates and polyesters are already used. Further possible applications of the polycarbonates according to the invention are:

1. Safety panes, which are known to be required in many areas of buildings, vehicles and aircraft, and as identification plates of helmets.
2. Production of films and film laminates.
3. Automobile headlamps, bezels, indicators, reflectors.
4. As translucent plastics having a content of glass fibres for lighting purposes, as translucent plastics having a content of barium sulphate, titanium dioxide and/or zirconium oxide
5. For the production of precision injection moulded parts, such as, for example, lenses, collimators, lens holders, waveguide elements and LED applications.
6. As electrical insulation materials for electrical conductors and for plug housings and connectors.
7. Housings for electrical devices.
8. Safety goggles, visors.
9. Extruded mouldings, such as sheets and films.
10. LED applications (bases, reflectors, heat sinks).

This application also relates to the mouldings or shaped articles and extrudates comprising the polymers according to the invention.

The following examples serve for further explanation of the invention.

All the references described above are incorporated by reference in their entireties for all useful purposes.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

EXAMPLES

The copolycarbonates were characterized by means of the Vicat temperature and the relative solution viscosity $\eta_{rel}$. Furthermore, the copolymers were investigated with regard to their coefficients of linear thermal expansion.

Determination of the Vicat Temperature and of the Relative Solution Viscosity

The Vicat temperature VST B50 is determined according to DIN ISO 306, method B, at a heat load of 50 K/h. The relative solution viscosity was determined in methylene chloride as a solvent at a concentration of 0.5 g/l and at a temperature of 25° C. using an Ubbelohde viscometer (DIN 51562).

Determination of the Coefficients of Linear Thermal Expansion:

The coefficients of linear thermal expansion are determined by means of a Mettler TMA 841 measuring apparatus under nitrogen (measuring range 23-55° C.). The standard used is ASTM E 831. The test specimens required for the measurement (flat bar 80×10×4 mm) are produced by injection moulding after drying of the pellets at 130° C. overnight. Measurement is effected in each case across and along the test specimen.

Example 1

The synthesis of the monomer building block according to the invention is effected according to FIG. 1.

A solution of 2 kg (20.2 mol) of N-methylpyrrolidone (NMP) and 1273.3 g (4 mol) of phenolphthalein is initially introduced into a reactor having a plane ground joint. With stirring, 2 liters of water and then 18 mol of a 40% strength aqueous methylamine solution are added. On addition of the methylamine, the reaction solution acquires a violet discoloration. With the use of a dry ice cooler, stirring is then continued for 8 hours at 82° C. The colour of the reaction batch changes to dark yellowish. After the end of the reaction, the reaction batch is precipitated by means of a dropping funnel with stirring in a vessel of water containing hydrochloric acid.

The precipitated white reaction product is suspended with 2 liters of water and then filtered with suction by means of a G3 frit. The crude product obtained is dissolved again in 3.5 liters of a dilute sodium hydroxide solution (16 mol) and precipitated again in a vessel of water containing hydrochloric acid. The reprecipitated crude product is suspended several times with 2 liters of water and then filtered with suction each time. This wash procedure is repeated until the conductivity of the wash water is less than 15 µS.

The product thus obtained is dried to constant mass at 90° C. in a vacuum drying cabinet.

In each case the following yields are obtained after the experiment has been carried out 4 times:
1a) 950 g of a white solid
1b) 890 g of a white solid
1c) 1120 g of a white solid
1d) 1050 g of a white solid The melting point determination of the product gave 264° C.

The characterization of the bisphenol obtained was effected by means of $^1$H-NMR spectroscopy.

Example 2

Synthesis of the Copolycarbonate According to the Invention 11.79 liters of methylene chloride and 14.1 liters of chlorobenzene are added to a solution made inert with nitrogen and comprising 532.01 g (1.6055 mol) of bisphenol A (BPA), 2601.36 g (11.39 mol) of bisphenol, from example 1, 93.74 g (0.624 mol, 4.8 mol %, based on diphenols) of p-tert.-butylphenol (BUP) as a chain terminator and 1196 g (29.9 mol) of sodium hydroxide in 25.9 liters of water. At a pH of 12.5-13.5 and 20° C., 2.057 kg (20.8 mol) of phosgene are passed in. In order to prevent the pH from falling below 12.5, 30% strength sodium hydroxide solution was added during the phosgenation. After the end of the phosgenation and flashing with nitrogen, stirring is effected for 30 minutes and 14.7 g (0.13 mol, 1 mol %, based on diphenols) of N-ethylpiperidine are then added as a catalyst and stirring is continued for 1 hour. After removal of the aqueous phase and acidification with phosphoric acid by means of a separator, the organic phase is washed salt-free several times with water. The organic phase is separated off and is subjected to a solvent exchange in which methylene chloride is replaced by chlorobenzene. The concentrated copolycarbonate solution in chlorobenzene is then freed from the solvent with the aid of a vented extruder. The polycarbonate melt extrudates obtained are cooled in a water bath, drawn off and finally pelletized.

Transparent polycarbonate pellets are obtained (for analysis, see Table 1).

Examples 3 to 5

Further Synthesis Examples for Copolycarbonates According to the Invention

The copolycarbonates of Examples 3 to 5 were prepared analogously to Example 2 (for results, see Table 1).

TABLE 1

| Copolycarbonate comprising | Example 5 | Example 4 | Example 3 | Example 2 |
|---|---|---|---|---|
| Bisphenol from Example 1 | | | | |
| [mol %] | 55.5 | 25.0 | 18.0 | 12.4 |
| [% by weight] | 62.2 | 32.6 | 24.2 | 17.0 |
| Bisphenol A (BPA) | | | | |
| [mol %] | 44.5 | 75 | 82 | 87.6 |
| [% by weight] | 37.8 | 67.4 | 75.8 | 83 |
| Vicat temperature [° C.] | 228.2 | 188.3 | 177.4 | 168.6 |
| Glass transition temperature Tg [° C.] | 230.0 | 189.9 | 178.9 | 168.7 |
| $\eta_{rel}$ | 1.235 | 1.240 | 1.237 | 1.238 |

Apec® samples (Bayer MaterialScience AG, Germany) having the Vicat temperatures stated in Table 2 are used as comparative samples. These represent the closest prior art for polycarbonates in high temperature applications.

TABLE 2

| Comparative examples | 6 | 7 | 8 | 9 |
|---|---|---|---|---|
| Vicat temperature [° C.] | 158 | 173 | 183 | 203 |
| Glass transition temperature Tg [° C.] | 157.2 | 169.9 | 179.3 | 204 |
| Coefficient of expansion Transverse [10$^{-6}$/K] | 68.0 | 68.0 | 66.0 | 66.0 |
| Coefficient of expansion Longitudinal [10$^{-6}$/K] | 67.0 | 67.0 | 67.0 | 64.0 |
| Sample according to the invention from example | 2 | 3 | 4 | 5 |
| Vicat temperature [° C.] | 168.6 | 177.4 | 188.3 | 228.2 |
| Coefficient of expansion Transverse [10$^{-6}$/K] | 65.0 | 63.4 | 63.4 | 59.7 |
| Coefficient of expansion Longitudinal [10$^{-6}$/K] | 63.1 | 64.0 | 62.8 | 59.4 |

In comparison with Comparative examples 6-9, it is found that the copolycarbonates according to the invention from Examples 2-5 have significantly lower values for the coefficients of thermal expansion at comparative Vicat temperatures. This was unexpected for the person skilled in the art. In particular the copolycarbonate from Example 5, with a Vicat temperature of 228.2° C., meets all necessary requirements with regard to reflector materials as far as thermal stability and reduced coefficient of expansion are concerned.

Thermal and Mechanical Properties:

The rheological properties were determined via the melt volume flow rate (MVR) according to ISO 1133.

The mechanical properties were determined via tensile modulus, stress at yield, strain at yield and nominal elongation at break according to ISO 527-1, -2, Charpy impact strength according to ISO 179-1 eU and Charpy notched impact strength according to ISO 179-1 eA.

The thermal properties were determined via heat deflection temperature HDT (A and B) according to ISO 75-1, -2 and via the Vicat softening temperature according to ISO 306.

Table 3 shows a complete overview of all thermal and mechanical properties of the copolycarbonates according to the invention in comparison with comparative samples having a similar Vicat temperature. It can be seen that the mechanical properties of the materials according to the invention from Example 2-5 show no deterioration compared with Comparative samples 1-4. As shown in Table 2 above, however, they have the advantage of lower coefficients of linear thermal expansion.

Moreover, the samples according to the invention show better flow behaviour in comparison with samples not according to the invention and having the same Vicat temperature (cf. Examples 2 and 6 or 3 and 7).

The invention claimed is:

1. A multilayer product comprising a substrate layer comprising a further layer at least on one side, wherein said substrate layer comprises a (co)polycarbonate comprising a bisphenol of formula (Ia) as a repeating monomer unit and one or more diphenols of formula (II) as repeating monomer units in said (co)polycarbonate

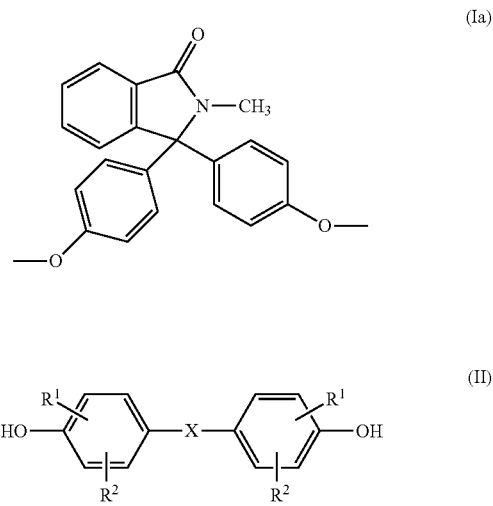

wherein
$R^1$ and $R^2$ are, independently of one another, hydrogen or $C_1$-$C_{18}$-alkyl, and

TABLE 3

|  |  | Comparative samples | | | | Samples according to the invention | | | |
| --- | --- | --- | --- | --- | --- | --- | --- | --- | --- |
|  |  | 6 | 7 | 8 | 9 | 2 | 3 | 4 | 5 |
| Mn |  | 10150 | 10544 | 9977 | 11456 | 9092 | 10004 | 9629 | 10328 |
| Mw |  | 25370 | 26253 | 26424 | 29061 | 22291 | 23228 | 24153 | 24257 |
| D |  | 2.50 | 2.49 | 2.65 | 2.59 | 2.45 | 2.32 | 2.51 | 2.35 |
| Eta rel |  | 1.257 | 1.253 | 1.249 | 1.248 | 1.238 | 1.238 | 1.241 | 1.235 |
| 1st measurement-2nd heating | ° C. | 156.7 | 169.9 | 180.8 | 204 | 168.6 | 178.5 | 190.1 | 230.1 |
| 2nd measurement-2nd heating | ° C. | 157.7 | 169.9 | 177.8 | 204 | 168.8 | 179.2 | 189.6 | 229.9 |
| Average temperature | ° C. | 157.2 | 169.9 | 179.3 | 204.0 | 168.7 | 178.9 | 189.9 | 230.0 |
| Melt volume flow rate (MVR) (330° C.; 2.16 kg) | cm³ (10 min) | 45 | 24 | 18 | 8 | 46.0 | 31.0 | 17.2 | 2.2 |
| Tensile modulus (1 mm/min) | MPa | 2400 | 2400 | 2400 | 2400 | 2407 | 2487 | 2532 | 2774 |
| Stress at yield (50 mm/min) | MPa | 68 | 72 | 74 | 76 | 70.6 | 73.8 | 77.7 | 92.5 |
| Strain at yield (50 mm/min) | % | 6.2 | 6.4 | 6.8 | 6.9 | 6.6 | 6.8 | 7.1 | 7.7 |
| Nominal elongation at break (50 mm/min) | % | 96 | 89 | 89 | 57 | 78 | 77 | 61 | 15 |
| Charpy impact strength (23° C.) | T kJ/m² | — | — | — | — | — | — | — | — |
|  | B | — | — | — | — | — | — | — | — |
|  | N | 10 × NB | 10 × NB | 10 × NB | 10 × NB | 10 × NB | 10 × NB | 10 × NB | 10 × NB |
| Charpy impact strength (−20° C.) | T kJ/m² | — | — | — | — | — | — | — | — |
|  | B | — | — | — | — | — | — | — | — |
|  | N | 10 × NB | 10 × NB | 10 × NB | 10 × NB | 10 × NB | 10 × NB | 10 × NB | 10 × NB |
| Charpy notched impact strength (23° C.; 3.0 mm) | kJ/m² | 10 × 13b | 10 × 12b | 10 × 10b | 10 × 8b | 10 × 16b | 10 × 17b | 10 × 16b | 10 × 17b |
| Heat deflection temperature HDT, Af (1.80 MPa) | ° C. | 138 | 149 | 158 | 173 | 144.9 | 154.1 | 164.1 | 201.6 |
| Heat deflection temperature HDT, Bf (0.45 MPa) | ° C. | 150 | 163 | 173 | 192 | 158.9 | 167.8 | 178.6 | 218.1 |
| Vicat softening temperature (50 N, 120 K/h) | ° C. | 158 | 173 | 183 | 203 | 168.6 | 177.4 | 188.3 | 228.2 |

T: tough
B: brittle
N: not broken
NB: not broken
b: brittle

X is a single bond or isopropylidene, wherein said substrate layer comprises a (co)polycarbonate comprising from 12 to 55 mol % of a bisphenol of formula (Ia) as a repeating monomer unit and from 88 to 45 mol %, based in each case based on the sum of diphenols used, of one or more diphenols of formula (II) as repeating monomer units in said (co)polycarbonate, and wherein said (co)polycarbonate further comprises one or more diphenols selected from diphenols of formula (IV), wherein said diphenols of formula (IV) is an isomer mixture of diphenols of formulae (IVa) and (IVb)

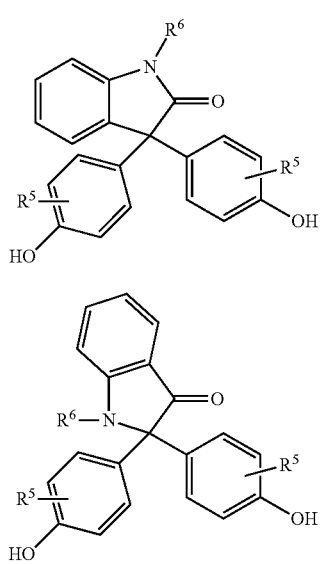

wherein
$R^5$ is, independently of one another, hydrogen or $C_1$-$C_{10}$ alkyl, and $R^6$ is $C_1$-$C_{10}$ alkyl or optionally substituted phenyl or benzyl.

2. The multilayer product of claim 1, wherein said further layer on said substrate layer is a metal layer.

3. The multilayer product of claim 2, further comprising a protective layer applied to said metal layer.

4. A process for producing the multilayer product of claim 3, comprising the step of applying said protective layer in a PECVD or plasma polymerization process.

5. The process of claim 4, comprising the step of applying said protective layer in a PECVD or plasma polymerization process from one or more readily volatile components selected from the group consisting of hexamethyldisiloxane (HMDSO), hexamethyldisilazane (HMDS), tetramethyldisiloxane, decamethylcyclopentasiloxane, octamethylcyclotetrasiloxane, and trimethoxymethylsilane.

6. The multilayer product of claim 2, wherein said metal layer is an aluminium layer.

7. The multilayer product of claim 2, wherein said metal layer has a thickness from 20 to 500 nm.

8. The multilayer product of claim 2, wherein the (co)polycarbonate is transparent.

9. The multilayer product of claim 1, wherein said diphenols of formula (II) are selected from the group consisting of bisphenol A, 4,4'-dihydroxybiphenyl, and 2,2-bis(3-methyl-4-hydroxyphenyl)propane.

10. The multilayer product of claim 1, wherein said (co)polycarbonate further comprises one or more additives selected from the group consisting of heat stabilizers, demoulding agents, UV absorbers, and fillers.

11. The multilayer product of claim 1, wherein said substrate layer comprises a (co)polycarbonate comprising from 45 to 55 mol % of a bisphenol of formula (Ia) as a repeating monomer unit and from 55 to 45 mol %, based in each case based on the sum of diphenols used, of one or more diphenols of formula (II) as repeating monomer units in said (co)polycarbonate.

12. The multilayer product of claim 1, wherein the (co)polycarbonate is transparent.

* * * * *